United States Patent
Oakley et al.

(10) Patent No.: US 10,279,118 B2
(45) Date of Patent: May 7, 2019

(54) DRIVE MECHANISM

(71) Applicant: Sanofi, Paris (FR)

(72) Inventors: Tom Oakley, Cambridge (GB); Matt Schumann, Cambridge (GB); Mark Pawulski, Buckingham (GB)

(73) Assignee: Sanofi, Paris (FR)

( * ) Notice: Subject to any disclaimer, the term of this patent is extended or adjusted under 35 U.S.C. 154(b) by 567 days.

(21) Appl. No.: 14/905,078

(22) PCT Filed: Jul. 17, 2014

(86) PCT No.: PCT/EP2014/065329
§ 371 (c)(1),
(2) Date: Jan. 14, 2016

(87) PCT Pub. No.: WO2015/007810
PCT Pub. Date: Jan. 22, 2015

(65) Prior Publication Data
US 2016/0151579 A1    Jun. 2, 2016

(30) Foreign Application Priority Data

Jul. 17, 2013 (EP) ..................... 13176852

(51) Int. Cl.
A61M 5/20 (2006.01)
A61M 5/315 (2006.01)
A61M 5/31 (2006.01)

(52) U.S. Cl.
CPC .......... A61M 5/31551 (2013.01); A61M 5/20 (2013.01); A61M 5/31535 (2013.01);
(Continued)

(58) Field of Classification Search
CPC ...... A61M 5/31535; A61M 2005/3154; A61M 5/31541; A61M 2005/3125; A61M 2005/3126
See application file for complete search history.

(56) References Cited

U.S. PATENT DOCUMENTS

| 8,048,037 B2 | 11/2011 | Kohlbrenner et al. |
| 2003/0160072 A1 | 8/2003 | Geiser et al. |
| (Continued) | | |

FOREIGN PATENT DOCUMENTS

| EP | 1 322 355 | 7/2003 |
| EP | 1 351 732 | 10/2003 |
| (Continued) | | |

OTHER PUBLICATIONS

International Preliminary Report on Patentability in International Application No. PCT/EP2014/065329, dated Jan. 19, 2016, 8 pages.
(Continued)

Primary Examiner — Nathan R Price
Assistant Examiner — Courtney B Fredrickson
(74) Attorney, Agent, or Firm — Fish & Richardson P.C.

(57) ABSTRACT

A drive mechanism (11) for a delivery device comprising a drive member (17) for driving a piston rod (13); a moveable dose setting member (19, 35) being disengaged from the drive member (17) in a dose setting state and being moveable in a drive direction in a dose delivery state, wherein the dose setting member (19, 35) engages with the drive member (17) in the dose delivery state in such a manner that the movement of the dose setting member (19, 35) in the drive direction is transferred to the drive member (17); and a spring member (21) being coupled to the dose setting member (19, 35) in such a manner that the movement of the dose setting member (19, 35) in a setting direction loads the spring member (21) in the dose setting state, the spring force of the loaded spring member (21) driving the dose setting member (19, 35) in the drive direction in the dose delivery state.

17 Claims, 10 Drawing Sheets

(52) U.S. Cl.
CPC .... *A61M 5/31536* (2013.01); *A61M 5/31553* (2013.01); *A61M 5/31578* (2013.01); *A61M 5/31583* (2013.01); *A61M 2005/3126* (2013.01)

(56) References Cited

U.S. PATENT DOCUMENTS

| | | |
|---|---|---|
| 2004/0054326 A1 | 3/2004 | Hommann et al. |
| 2009/0082727 A1* | 3/2009 | Moeller ............ A61M 5/14224 604/132 |
| 2009/0254035 A1 | 10/2009 | Kohlbrenner et al. |
| 2009/0254048 A1 | 10/2009 | Hetherington |
| 2011/0004166 A1* | 1/2011 | Wittmann ............... A61M 5/20 604/207 |
| 2012/0253287 A1 | 10/2012 | Giambattista et al. |

FOREIGN PATENT DOCUMENTS

| | | |
|---|---|---|
| JP | 2008-504919 | 2/2008 |
| JP | 2010-503430 | 2/2010 |
| JP | 2013-513459 | 4/2013 |
| WO | WO 2002/076535 | 10/2002 |
| WO | WO 2006/079481 | 8/2006 |
| WO | WO 2010/046394 | 4/2010 |

OTHER PUBLICATIONS

International Search Report and Written Opinion in International Application No. PCT/EP2014/065329, dated Oct. 24, 2014, 11 pages.

\* cited by examiner

DRIVE MECHANISM

CROSS-REFERENCE TO RELATED APPLICATIONS

This application is a U.S. national stage application under 35 USC § 371 of International Application No. PCT/EP2014/065329, filed on Jul. 17, 2014, which claims priority to European Patent Application No. 13176852.5, filed on Jul. 17, 2013, the entire contents of which are incorporated herein by reference.

The invention concerns a drive mechanism for a delivery device, in particular a drug delivery device.

In a delivery device, a bung within a cartridge that contains a liquid or a paste may be displaced by a piston rod, thereby delivering a dose of the content of the cartridge. The delivery device comprises a drive mechanism which allows setting and delivering the dose by means of piston rod movement. During the dose setting phase, the piston rod is not moved distally; in the dose delivery phase, it is. Such a delivery device may be formed as a drug delivery device suitable for delivering a liquid drug.

Documents WO 2010/046394, WO 2006/079481, EP 1351732, and EP 1322355 show drug delivery devices.

Most pen injectors have a dosage selector which rotates on the same axis as the cartridge and, on the end opposite to the needle, a button which moves along the same axis as the axis of the cartridge.

Some injection devices have a dosage selector on the front of the device which rotates on an axis perpendicular to that of the cartridge.

The disadvantage of placing the button on the end opposite to the needle and moving the same in the direction of the cartridge's axis is that some users may find it difficult to extend their thumb to the button position and exert the required force.

Many injection devices fall into the following categories: manually-driven devices, spring-driven devices, and motor-driven devices.

The motors of motor-driven devices may be expensive. Moreover, the motors may be heavy, which renders drop testing challenging. Furthermore, the motors require a power supply such as batteries, which adds further to cost, weight and environmental impact on disposal. Motors normally require electronic control systems, which increase the cost, complexity, regulatory challenge, and environmental impact on disposal.

The problems with manual devices are that, in manual devices, the force for driving the piston rod is exerted by the user during dose delivery. The amount of energy required to inject e.g. 120 IU of U300 insulin formulation may be not available from the thumb with an acceptable force and displacement for usability. Then again, the user may press the button too hard, leading to a fast injection, which requires a longer hold time after the device has injected the drug before the user can retract the needle from the skin. Users might not keep the needle in place for this increased hold time and therefore receive an under-dose.

For these reasons, spring-driven devices can be attractive. It is an aim of the invention to provide a drive mechanism having spring support.

A drive mechanism for a delivery device, in particular a drug delivery device, is provided. The drive mechanism comprises a drive member for driving a piston rod and a moveable dose setting member being disengaged from the drive member in a dose setting state and being moveable in a drive direction in a dose delivery state, wherein the dose setting member engages with the drive member in such a manner that the movement of the dose setting member in the drive direction is transferred to the drive member. The drive mechanism further comprises a spring member coupled to the dose setting member in such a manner that the movement of the dose setting member in a setting direction loads the spring member in the dose setting state, the spring force of the loaded spring member driving the dose setting member in the drive direction in the dose delivery state, thereby moving the drive member.

The term "piston rod" shall preferably mean a component adapted to operate through/within a housing of the delivery device, which may be designed to move axially through/within the delivery device, for example for the purpose of discharging/dispensing an injectable product. "Piston rod" shall further mean a component having a circular or non-circular cross-section. It may be made of any suitable material known by a person skilled in the art and may be of unitary or multipart construction.

A drive member may be configured to transfer force to the piston rod. The transferred force may cause the piston rod to be displaced in the distal direction for dose delivery.

The dose setting member is moveable in a first direction, i.e. the setting direction, thereby increasing the set dose, and in a second direction, i.e. the drive direction, thereby decreasing the set dose. The second direction may be opposite to the first direction. The first direction may be clockwise and the second direction may be counter-clockwise, for example. The dose setting member moves in the second direction in the dose delivery state.

The drive member and the dose setting member may be formed as gears, which disengage in the dose setting state in such a manner that the gears do not interact and no movement is transmitted to the drive member. The gears engage in the dose delivery state. Such interlock causes transmission of movement from one component to the other.

The spring member is an elastic object used to store mechanical energy. The spring member may be loaded by deflection, thereby storing sufficient energy for drug delivery. The stored energy drives, via the dose setting member and the drive member, the piston rod in the dose delivery state. The spring may be biased or pre-stressed in the initial state, which ensures that the components are placed in good fit and/or that the device can provide enough force to perform an injection even if a minimum dose volume is set.

In comparison with a manually-driven mechanism, the spring-loaded drive mechanism requires little injection trigger force because of the energy-storing spring member.

The components may be coupled directly, e.g. by being connected or engaged, or indirectly, i.e. by means of other components. Components that are coupled may or may not be able to move, e.g. axially and/or rotationally, with respect to each other.

The drive mechanism preferably comprises a ratchet means preventing movement of the dose setting member in the drive direction, which is caused by the spring force in the dose setting state. The ratchet means allows motion in the setting direction during the dose setting state. Preferably, the ratchet means also allows movement in the drive direction, which is caused by the user in the dose setting state. Such configuration allows increasing and decreasing the dose in the dose setting state while preventing movement caused by the loaded spring member in the dose setting state. The manually impacted force for dose setting overcomes the spring force, which is blocked by the ratchet means, thereby allowing dose setting though the ratchet means is provided. The ratchet means may be formed as spring-loaded teeth or a spring-loaded finger engaging with the dose setting member. Such spring-load may be caused by the elasticity of the material of the ratchet means.

The dose setting member may comprise a floating gear being suitable for engaging with the drive member. A gear is a rotating machine part having cut teeth, or cogs, which mesh with another toothed part in order to transmit torque. Such a gear may be a gear with radially projecting teeth, e.g. a toothed wheel.

The spring member may comprise a flat torsion spring. A torsion spring is a spring that works by torsion or twisting. It stores mechanical energy when it is twisted. When being twisted, it exerts a force, i.e. torque, in the opposite direction, proportional to the angle, to which it is twisted. One embodiment of the spring member may be a spiral spring made of a spiral-formed wire running in a plane. A flat torsion spring is constructed from a flat sheet material, e.g. a ribbon or strip having a rectangular or ellipsoid cross-section and being helically-shaped or spirally-shaped. Such a non-wire torsion spring is made of a flat shaped material not having a round cross-section. The torsion spring may be made of, for example, metal and/or plastic.

The dose setting member may comprise a further gear, wherein the flat torsion spring is arranged adjacent to a face side of the further gear, which allows a flat design. The second gear may be a gear having a larger diameter than the floating gear.

The floating gear is moveable along its rotation axis with respect to the further gear in such a manner that the floating gear disengages from the drive member in the dose setting state and engages with the drive member in the dose delivery state. Such movement may be initiated by a simple switch mechanism.

The drive member may comprise a drive gear which may be driven by the rotation dose setting member. The drive member may be coupled to the piston rod by a rack-and-pinion means, which comprises a pair of gears which convert rotational motion into linear motion. A circular gear, i.e. the pinion, engages teeth on a linear gear bar, i.e. the toothed rack; rotational motion applied to the pinion causes the rack to move, thereby translating the rotational motion of the pinion into the linear motion of the rack. The pinion may be part of or connected with the drive member or the drive gear; the rack may be part of or connected to the piston rod. Such a rack-and-pinion means transfers the rotation of the drive member to a distal movement of the piston rod in the dose delivery state.

The drive mechanism may comprise a rotatable dosage selector coupled to the dose setting member in such a manner that a rotational movement of the dosage selector may be transferred to the dose setting member in the dose setting state. Such coupling may be achieved by means of toothed gears, for example.

The dosage selector may be coupled to a units wheel and a tens wheel, the latter being coupled to the units wheel by an escapement gear; the units wheel indicating the units of the set dose; the tens wheel indicating the tens of the set dose. When the units wheel makes one revolution, the tens wheel moves only one increment. The units and tens wheels form a dosage indicator.

A button member may be coupled to the dose setting member in such a manner that pressing the button causes engagement of the dose setting member with the drive member. In other words, the button member allows switching from the dose setting state to the dose delivery state.

A lever arm may serve as a switching means, the lever arm being suitable to move the first gear such that it engages with the drive member when the button is pressed.

The ratchet means may be connected to the lever; the ratchet means engages with the dose setting member in the dose setting state, thereby preventing the spring force from moving the units wheel. Nevertheless, manually initiated movement of the dose setting member during the dose setting process is possible. The lever arm not only moves the floating gear but also disengages the ratchet means when the button is pressed.

The drive mechanism may further comprise a dose control means that is coupled to the dose setting member in such a manner that the dose setting member is blocked when a maximum or minimum dose is set, and a further ratchet means preventing transmission of movement from the dosage selector to the dose setting member when the dose setting member is blocked. This mechanism helps prevent over-dosage or under-dosage.

The drive mechanism may comprise at least one dose setting wheel being suitable for providing tactile and/or audible feedback which is formed as to their position or movement.

In one embodiment the button member is located axisymmetrically with the dose setting member.

The drive mechanism as described above may be used in a delivery device, preferably a drug delivery device. The housing of such a delivery device may comprise an upper case and a lower case. In one embodiment the upper case and the lower case are joined along a substantially planar interface, wherein the normal to that plane is more than 45 degrees from the axis of the cartridge. Preferably the normal is substantially orthogonal to the axis of the cartridge.

The terms "drug", "medicament" or "medication", as used herein, preferably mean a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropin (Follitropin, Lutropin, Choriongonadotropin, Menotropin), Somatropin (Somatropin), Desmopressin, Terlipressin, Gonadorelin, Triptorelin, Leuprorelin, Buserelin, Nafarelin, Goserelin.

A polysaccharide is for example a glucosaminoglycan, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies will become apparent from the following description of the exemplary embodiments in connection with the figures.

FIG. 1 shows a three-dimensional back view of a delivery device, that may be a drug delivery device, the lower case (not shown) of the housing being removed for showing the inside of the delivery device.

Figure 1:
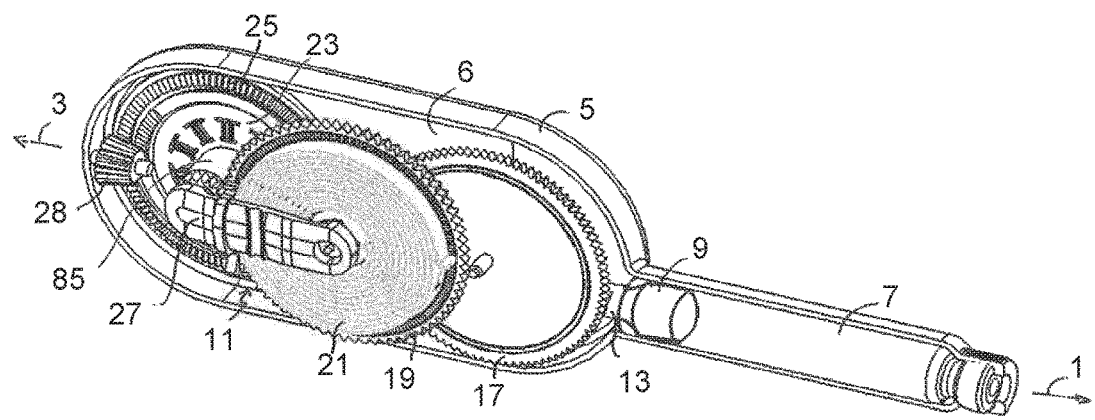
FIG. 1 shows a three-dimensional back view of a delivery device including a drive mechanism.

The delivery device has a distal end and a proximal end. The term "distal end" of the delivery device or a component thereof may refer to that end of the device or the component which is closest to the dispensing end of the device. The term "proximal end" of the delivery device or a component thereof may refer to that end of the device or the component which is furthest away from the dispensing end of the device. The distal direction is indicated by an arrow 1. The proximal direction is indicated by an arrow 3.

The delivery device is based on a flat odometer injector concept featuring a front-mounted dosage selector and injection button (not shown in FIG. 1), and a rack-and-pinion drive mechanism. The delivery device may be used to inject a liquid drug or medicament such as insulin. This may be for human use. Alternatively, the delivery device may be used for non-insulin formulations.

The delivery device comprises a housing 5. The term "housing" shall preferably mean any exterior housing ("main housing", "body", "shell") or interior housing ("insert", "inner body") which may have a unidirectional axial coupling to prevent proximal movement of specific components. The housing may be designed to facilitate the safe, correct and comfortable handling of the medication delivery device or any of its mechanisms. Usually, it is designed to house, fix, protect, guide, and/or engage with any of the inner components of the delivery device (e.g. the drive mechanism, cartridge, piston rod), preferably by limiting the exposure to contaminants, such as liquid, dust, dirt etc. In general, the housing may be a unitary or a multipart component of tubular or non-tubular shape. In this embodiment, the housing 5 is asymmetric. The housing includes a lower case (not shown) covering the back of the delivery device and an upper case 6 covering the front of the delivery device.

A cartridge 7 is located inside the distal part of the housing 5, which serves as a cartridge holder. The cartridge 7 contains a liquid drug or medicament; it has a distal end covered by a membrane that may be punctured by a needle (not shown) for delivery. A bung 9 is located at the proximal end of the cartridge 7, the bung 9 being moveable distally along the inner side wall of the cartridge 7, thereby reducing the volume of the drug-containing chamber of the cartridge 7 so that the drug is ejected through the needle (not shown). The cartridge 7 may be held in its position by parts of the interior housing 5 in such a manner that the distal end of the cartridge 7 is located at a distal opening of the housing 5, which allows attachment of the needle to the cartridge 7 or the housing 5. Alternatively, the cartridge 7 is mainly held by other components in its position. The delivery device may be intended to accept a 1.5 ml cartridge 7 or a 3.0 ml cartridge 7, but the design may also be adapted to accept containers of different sizes or formats. A detachable cap (not shown) may be provided for protection of the distal part of the delivery device.

A drive mechanism 11 is located inside the housing 5, this drive mechanism 11 being suitable for moving the bung 9 inside the cartridge 7 in the distal direction, thereby delivering the liquid.

The drive mechanism 11 comprises a piston rod 13 having a distal end which abuts on the bung 9. The piston rod 13 is moveable in the distal direction with respect to the housing 5 and the cartridge 7, thereby moving the bung 9 distally, which causes delivery. The piston rod 13 may have a rectangular or circular cross section. The piston rod 13 may be stiff along its major axis but flexible in other directions such that it can deflect away from its axis, for example to bend. In the present embodiment, the piston rod 13 is rather flat and has a rectangular cross section.

The drive mechanism is configured for transferring force to the piston rod 13 for displacing the bung 9 distally. A dose of liquid may be dispensed from the cartridge 7 in this way. The size of the delivered dose may be determined by the distance by which the piston rod 13 is displaced with respect to the cartridge 7.

The drive mechanism further comprises a drive gear 17, which is a toothed wheel, serving as a drive member for driving the piston rod 13 in the distal direction. The drive gear 17 is rotatable with respect to the housing 5 around an axis which does not move with respect to the housing 5. The drive gear 17 may be fixed to a shaft that is held between the upper case 6 and the lower case (not shown) in such a manner that it may rotate.

An idler gear 19 serving as a dose setting member is formed as a toothed wheel. The idler gear 19 is coupled with a spring member 21, which may be formed as a flat torsion spring, coupled to the idler gear 19 in such a manner that rotational movement of the idler gear 19 may deflect the spring member 21. The idler gear 19 is rotatable with respect to the housing 5 around an axis which does not move with respect to the housing 5. The idler gear 19 may be fixed to a shaft that is held between the upper case 6 and the lower case (not shown) in such a manner that it may rotate.

The drive mechanism 11 further comprises a units wheel 23 and a tens wheel 25 having symbols such as numbers or digits on their outer side, which allow indication of the set dose. The units wheel 23 may show the digits from 0 to 9. The tens wheel 25 may show the digits from 0 to 12. Thus, every number between 0 and 120 can be indicated. Exemplary digits may have a character height of 3.5 mm. The units and tens wheels 23, 25 are rotatable with respect to the housing 5 around a same axis which does not move with respect to the housing 5. The units wheel 23 and the tens wheel 25 are coupled by an escapement gear 28 in such a manner that the tens wheel 25 moves one increment, i.e. from one digit to the following digit, per one rotation of the units wheel 23. The rotation of the units wheel 23 is transferred to the idler gear 19 by teeth on a shaft 85 that is connected to the units wheel 23, the teeth engaging with the teeth of the idler gear 19.

Furthermore, the shaft of the button 47 is coupled via a lever arm 27 to the idler gear 19. Its function is described later.

Figure 2:
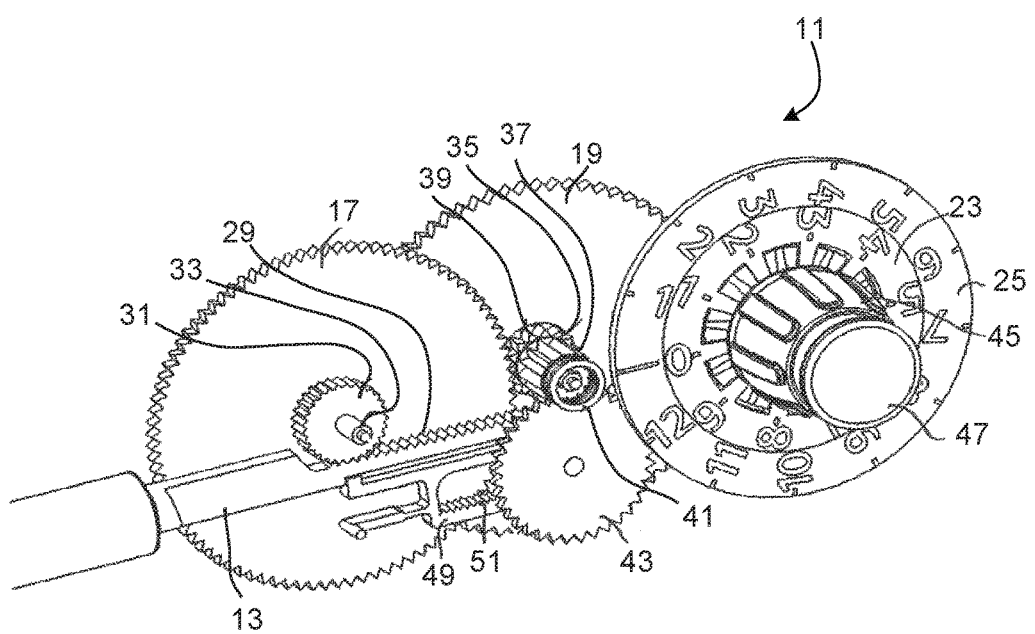
FIG. 2 shows a three-dimensional front view of the drive mechanism.

FIG. 2 shows a front view of the drive mechanism shown in FIG. 1. The housing 5 is not shown for clarity reasons.

The piston rod 13 comprises a toothed drive rack 29 that forms a rack-and-pinion system with a drive pinion 31, which is non-rotatably fixed to the drive gear 17 in such a manner that the drive pinion 31 and the drive gear 17 rotate around the same axis but do not rotate with respect to each other. The drive pinion 31 and the drive gear 17 may be connected by means of a shaft 33 coupled to the housing 5 in such a manner that the shaft 33 may rotate with respect to the housing 5. The drive pinion 31 and the drive gear 17 may be integrally formed. Rotation of the drive gear 17 may be transferred via the drive pinion 31 to the drive rack 29 of the piston rod 13, thereby moving the piston rod 13 distally for the purpose of liquid delivery.

The idler gear comprises a fixed idler gear 19 and a floating idler gear 35 that is non-rotatably coupled to the fixed idler gear 19 but is axially moveable with respect to the fixed idler gear 19. The floating idler gear 35 may slide along the fixed idler gear's rotation axis. The components 19, 35 may be coupled by a splined connection. The floating idler gear 35 includes a first toothed wheel 37 arranged on a second toothed wheel 39 that has a larger diameter than the first toothed wheel 37. The teeth of the first toothed wheel 37 do not engage with the teeth of the drive gear 17. After axially protruding the floating idler gear 35, the teeth of the second toothed wheel 39 are placed adjacent to the edge of the drive gear 17; thus, the teeth of the second toothed wheel 39 and of the drive gear 17 engage. This movement allows the coupling and decoupling of the idler gear 19, 35, which serves as dose setting member, and the drive gear 17, which serves as drive member. In one state (the dose delivery state), rotational movement of the fixed idler gear 19 is transferred by the floating idler gear 35 engaging with the teeth of the drive gear 17; in the other state (the dose setting state), the teeth of the floating idler gear 35 do not engage with the drive gear 17, and no rotation is transferred.

An idler spring 41, e.g. a helical spring, is placed between the floating idler gear 35 and the housing 5 (not shown) which biases the floating idler gear 35 in a state in which it does not engage with the drive gear 17.

The first toothed wheel 37 of the floating idler gear 35 engages with teeth of a dose gear 43, thereby allowing transferring rotational movement of the idler gear 19 to the dose gear 43, which is a toothed wheel. The components 37,

43 engage, irrespective of whether the second toothed wheel 39 engages with the drive gear 17 or not. The dose gear 43 is rotatable with respect to the housing 5 around an axis which does not move with respect to the housing 5.

A sleeve-shaped dosage selector 45 is coupled to the units wheel 23. On the face side of the dosage selector 45, an injection button 47 or button member is placed which may be pressed for initiating delivery. The dosage selector 45 and the injection button 47 protrude out of the housing 5 (not shown), which allows setting the desired dose by manually rotating the dosage selector 45. The dosage selector 45 may be thumb-operable. A button spring (not shown) may be located inside the dosage selector 45, the spring being deflected when the injection button 47 is pressed. When the injection button 47 is no longer pressed, the button spring (not shown) moves the injection button 47 back into its initial position. The button spring (not shown) may be a compression spring.

Moreover, the drive mechanism comprises a dose control means 49 including a dose rack 51 which is coupled via a dose pinion (not shown) to the dose gear 43 in such a manner that rotational movement of the dose gear 43 is transferred via the dose pinion to the rack 51, thereby travelling the dose control means 49 longitudinally along the piston rod 13.

Figure 3:
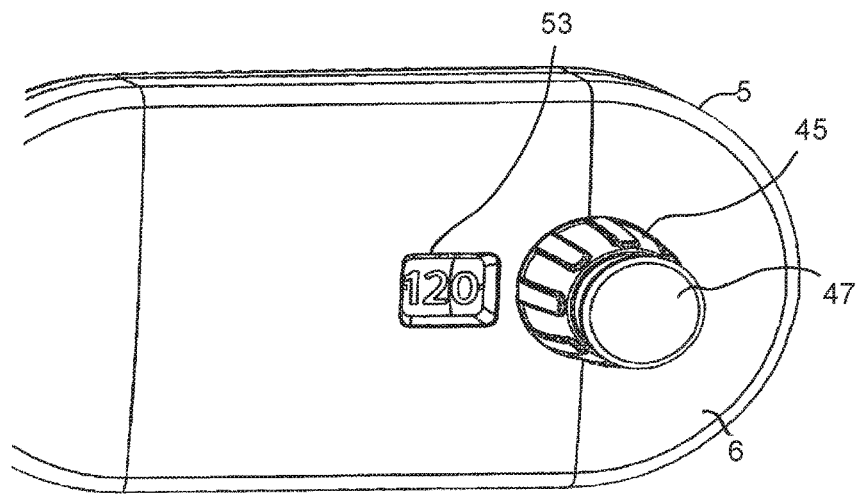
FIG. 3 shows a three-dimensional front view of the proximal part of the delivery device.

FIG. 3 shows a three-dimensional front view of the proximal part of the delivery device comprising the dosage selector 45 and the injection button 47.

The dose is set by rotating the dose selector 45, as a result of which the units and tens wheels 23, 25 rotate. Sections of the units and tens wheels 23, 25 are shown in a window 53 in the upper case 6 of the housing 5 forming a dose indicator. The digits shown in the window 53 indicate the amount of the set dose. A magnification lens (not shown) may be located in the window 53. In this embodiment, every unit is indicated. For example, in one embodiment, twelve rotations of the units wheel 23 are required to the set a maximum dose of 120 IU of insulin formulation.

The user sets the dose by rotating the dosage selector 45 anti-clockwise. The reason for rotating anti-clockwise is that the dose indicator, like most odometers, shows increasing numbers coming from above. If clockwise rotation is required, the internal mechanism could be mirrored. Most odometers feature high numbers rotating downwards from above. Such odometers include those used in car dashboards, or handheld counters used to count people.

The injection button 47 is positioned on the front of the device with its direction of movement non-parallel to the cartridge's axis. The flat odometer layout is more comfortable because the thumb is in a more natural position and the force required is more similar to a standard grip manoeuvre.

Figure 4:
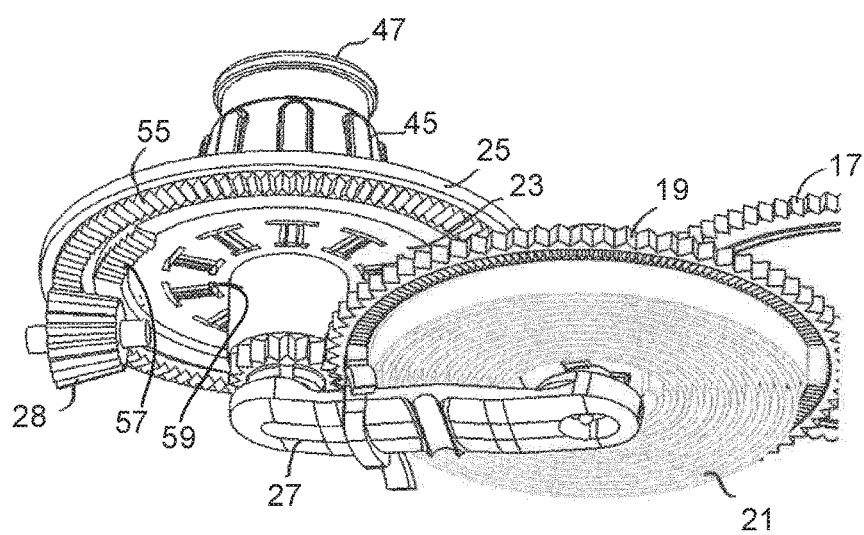
FIG. 4 shows a detailed three-dimensional view of an escapement mechanism and a lever arm of the drive mechanism.

FIG. 4 shows a detailed three-dimensional view of the escapement mechanism and the lever arm 27 coupling the injection button 47 and the idler gear 19, 35.

Rotating the dosage selector 45 rotates the units wheel 23 directly, although there is a torque-limiting ratchet between the dosage selector 45 and the units wheel 23 that allows relative rotation if the dose limits are reached. This feature is described later in connection with FIG. 9.

Returning to FIG. 4, the tens wheel 25 has a toothed ring 55 on its button face, which forms a crown gear being a driven rack. The units wheel 23 comprises a set of teeth 57 which are arranged along a circular arc on the button face. The set of teeth 57 serves as a drive rack. By means of an escapement gear 28 in the form of a conically shaped bevel gear, those teeth engage with the teeth 55 of the tens wheel 25. When the set of gear teeth 57 of the units wheel 23 moves along the escapement gear 28, those teeth engage with the teeth of the units wheel 23, thereby transferring the movement of the units wheel 23 to the tens wheel 25 until the set of teeth 57 has passed the escapement gear 28.

One rotation of the units wheel 23 causes only a stepwise movement of the tens wheel 25 by one increment. In other words, at every ten units of dose, the set of gear teeth 57 on the units wheel 23 engages the escapement gear 28. The rotation of the escapement gear 28 about its axis rotates the tens wheel 25 by one digit. The idea of this design is that the features (not shown) of the lower case 54 (not shown) which support the shaft of the escapement gear 28 will provide a small amount of friction to prevent the tens wheel 25 and the escapement gear 28 from rotating accidentally.

There are notch features 59 formed as protrusions, structures or ramps on the underside of the units wheel 23, which interact with ribs 61 (not shown) from the lower case 54 (not shown).

Figure 5:
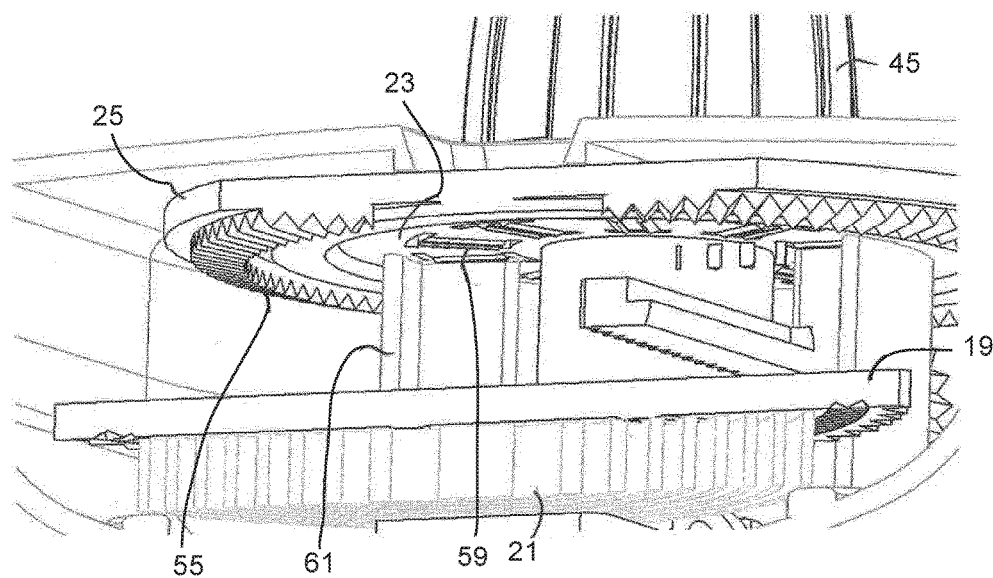
FIG. 5 shows a detailed three-dimensional view of this section showing ribs from a lower case interacting with notch features.

FIG. 5 shows a detailed three-dimensional view of this section showing the ribs 61 from the lower case 54 interacting with the notch features 59 on the underside of the units wheel 23.

When the notch features 59 interact with the ribs 61, the user feels a slight click feedback when the units wheel 23 lines up with a unit of dosage. The feedback may be predominantly tactile, although an audible click could be provided for if the design was required to. The notch features 59 could be designed to give the feedback at almost any position on the units wheel 23, but aligning one notch feature 59 per unit of dose is expected to be the most intuitive and therefore most useful and least confusing concept.

Figure 6:
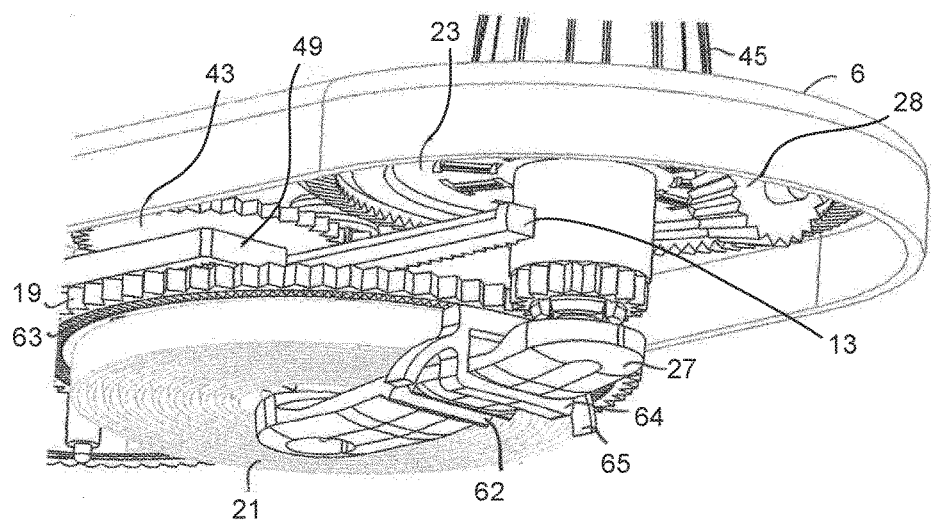
FIG. 6 shows an alternative detailed three-dimensional view of this section.

FIG. 6 shows an alternative detailed three-dimensional view of the section already shown in FIG. 4 including the lever arm 27.

The lever arm 27 is a movable bar that pivots on a fulcrum (not shown) attached to a fixed point. The fulcrum (not shown) may be formed as a protrusion of the housing 5 which engages with a recess 62 in the lever arm 27. If one end of the lever arm 27 is moved in a first direction, i.e. towards the lower case 54 (not shown), the other end of the lever arm 27 will move in a second direction opposite to the first direction, i.e. towards the upper case 6.

The injection button 47 is coupled via the lever arm 27 to the floating idler gear 35 in such a manner that pressing the injection button 47 causes axial movement of the floating idler gear 35 in the second direction, i.e. towards the upper case 6, which couples the second toothed wheel 39 to the drive gear 17. This movement causes deflection of the idler spring 41 (not shown). If the injection button 47 is no longer pressed, the deflected idler spring 41 (not shown) exerts a force on the floating idler gear 37, which then moves axially backwards, i.e. towards the lower case 54 (not shown), thereby disengaging the second toothed wheel 39 from the drive gear 17. Furthermore, the lever gear 27 and the injection button 47 move back to their initial positions.

The fixed idler gear 19 is coupled to the spring member 21, which may be formed as a flat torsion spring. A spring is an elastic object used to store mechanical energy. A torsion spring is a spring that works by torsion or twisting. It is a flexible elastic object that stores mechanical energy when it is twisted. When being twisted, it exerts a force, actually torque, in the opposite direction, proportional to the angle, of which it is twisted. One embodiment of the spring member 21 may be a flat spiral spring made of a spiral-formed wire. Such a torsion spring may be manufactured from essentially round wire.

Preferably, the flat spiral spring is made of a ribbon having a rectangular or ellipsoid cross-section. The torsion spring in this embodiment is constructed from a flat sheet material and has the following advantages over a wire spring. The force profile can be modified, e.g. based on the 'tensator' design concept known in mechanical engineering. The envelope of the non-wire spring can be much flatter than for a helical wire spring.

The spring member 21 may be deformed during assembly of the delivery device such that it exerts an appropriate force to effect delivery even when a minimum dose has been set.

The spring member 21 is deformed during the dose setting state of the delivery device in such a manner that it stores mechanical energy and at least partly relaxes during the delivery state of the device, thereby exerting a spring force on some of the components. This spring-loaded drive mechanism may be similar to the design of an auto-injector, which, however, can be used only once in contrast to the multi-dose delivery device as described. The spring-loaded drive mechanism has a low injection trigger force.

The spring member 21 is coupled to the idler gear 19, 35 in such a manner that the rotation of the idler gear 19 deforms the spring member 21. One end of the spring member 21 may be connected to the idler gear 19, 35; the other end of the spring member 21 may be connected to another component, e.g. the housing 5.

The fixed idler gear 19 comprises a crown gear 63, which is a gear that has teeth projecting towards the face of the wheel. A sprung idler ratchet 64 is connected to the lever arm 27. The idler ratchet 64 has teeth that engage with the teeth of the crown gear 63 if the injection button 47 and the lever arm 27 are in their initial positions. The idler ratchet 64 has legs 65, preferably made of an elastic material, which act as springs against the lower case 54 (not shown), thereby holding the idler ratchet 64 in its position. When the teeth of the idler ratchet 64 engage with the teeth of the crown gear 63, the units wheel 23 is prevented from rotating backwards under the torque from the spring member 21, because the teeth of the sprung idler ratchet 64 prevent the idler gear 19 from rotating back. Nevertheless, the idler ratchet 64 allows clockwise and counter-clockwise rotation of the fixed idler gear 19 in the dose setting state, even though the idler ratchet's 64 teeth engage with the crown gear 63. This configuration allows increasing and decreasing the dose in the dose setting state while preventing movement caused by the loaded spring member 21. In this case, the manually exerted force for dose setting may increase the spring force, which is blocked by the ratchet means, and the force of the holding idler ratchet 64. In other words, the idler ratchet 64 may serve as a torsion limiter, which does not transfer the torsion caused by the spring member 21 but transfers larger manually exerted torsion.

Figure 7:
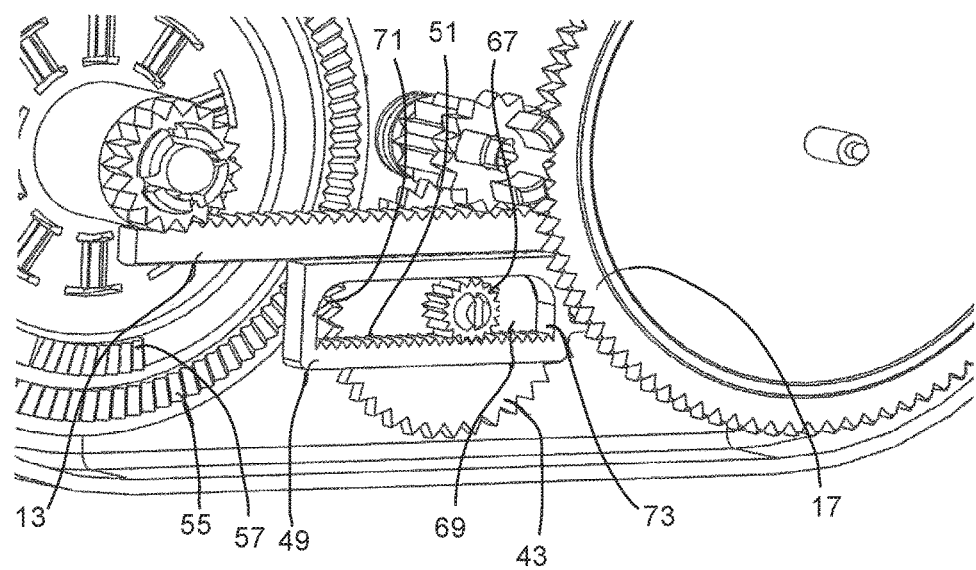
FIG. 7 shows a detailed three-dimensional back view of the dose control means and the neighbouring components.

FIG. 7 shows a detailed three-dimensional back view of the dose control means 49 and the components it interacts with. The dose control means 49 is an elongate component having a dose rack 51 with teeth, the dose rack 51 being formed in an elongate slot 69. A dose pinion 67 and the dose rack 51 form a rack-and-pinion means. The dose pinion 67 engages with the dose rack 51 in such a manner that the dose control means 49 and its dose rack 51 move along the dose pinion 67 when the latter rotates. The dose pinion 67 may be fixed to the dose gear 43 in a non-rotational manner. In one embodiment, the dose pinion and the dose gear 43 are integrally formed in one piece. The dose control means 49 comprises start and end stop means 71, 73 that are formed by side walls of the slot 69 located on either side of the dose rack 51.

When the dose is set, the units wheel 23 rotates the fixed idler gear 19 and therefore the dose gear 43, which moves the dose rack 51 linearly. The dose pinion 67 on the dose gear 43 runs inside the slot 69 in the dose control means 49. When the dose control means 49 reaches either a minimum dose position (for example, 0 IU of insulin formulation position) or a maximum dose position (for example, 120 IU of insulin formulation position), the dose pinion 67 comes up against a wall 71, 73 in the slot 69 and, as a result, prevents further rotation of the dose pinion 67 and thus the dose gear 43, the idler gear 19, 35 and the units wheel 23.

If a dose smaller than the maximum dose is set, the dose control means 49 travels without reaching the end stop means 73. Setting less than the minimum dose is not possible since such a movement will be stopped by the start stop means 71. During the dose delivery state, the dose control means 49 moves back until it reaches the start stop means 71.

The dose control means moves along the edge of the piston rod 13, which may guide the dose control means, ensuring longitudinal movement. In the dose setting state, the dose control means moves proximally with respect to and along the piston rod, which remains in its position. In the dose delivery state, the piston rod 13 and the dose control means 49 both move distally.

Figure 8:
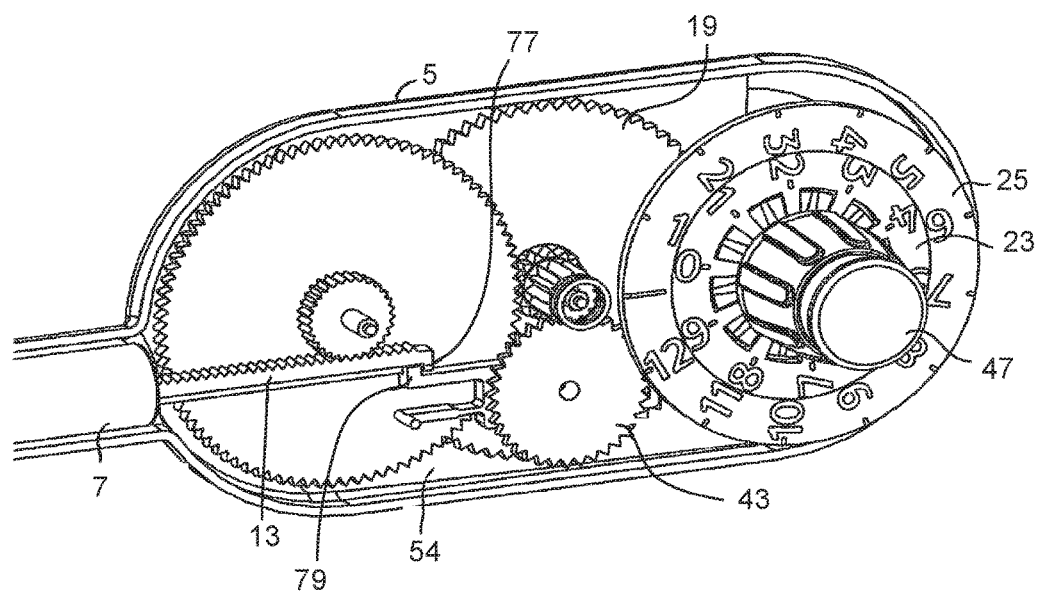
FIG. 8 shows a detailed three-dimensional front view of the drive mechanism.

FIG. 8 shows a detailed three-dimensional front view of the drive mechanism 11 in a state where there is less than the maximum dose left in the cartridge 7.

The dose control means 49 is moved with respect to the piston rod 13 during the dose setting state. The dose control means 49 and the piston rod 13 are coupled in such a manner that the travel of the dose control means 49 with respect to the piston rod 13 is limited. Such coupling may be achieved by a catching means 77 of the piston rod 13 engaging with a catching means 79 of the dose control means 49 when the dose control means 49 has reached a maximum travel with respect to the piston rod 13. The catching means 77 may be a finger or an edge abutting against a finger or an edge of the dose control means 49 when the maximum travel is reached. This engagement stops further travel of the dose control means 49 and limits the set dose.

When there is less than the maximum dose, e.g. 120 IU of insulin formulation, of liquid left in the cartridge 7, the piston rod 13 is extended to such a position that it limits the movement of the dose control means 49 and therefore limits the maximum settable dose to that remaining in the cartridge 7.

If the user tries to select a smaller or larger dose than permitted, the dosage selector 45 can nevertheless rotate relative to the units wheel 23 based on a torque-activated ratchet.

Figure 9:
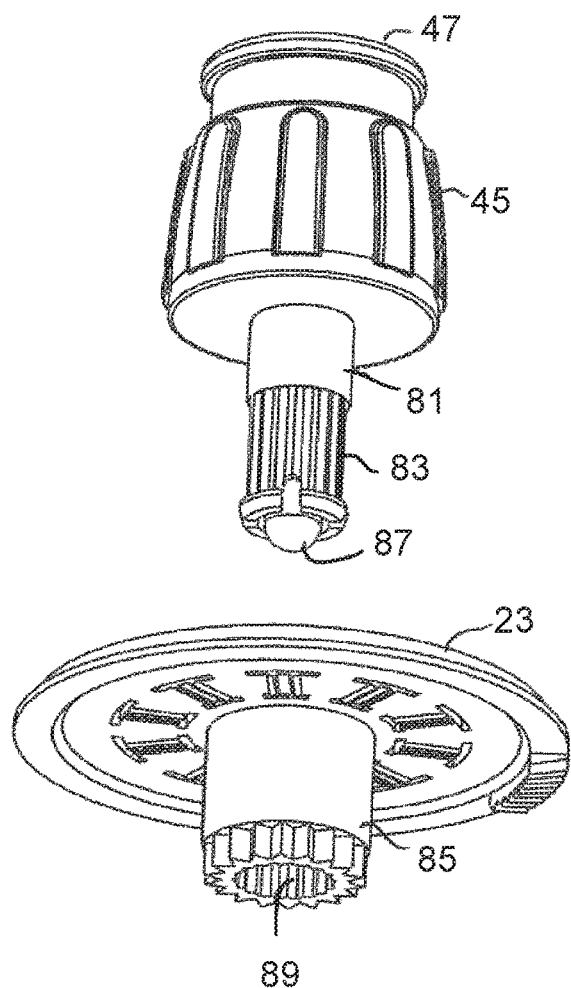
FIG. 9 shows a three-dimensional view of a dosage selector and a units wheel.

FIG. 9 shows a three-dimensional view of the dosage selector ratchet. The dosage selector 45 comprises a hollow shaft 81 having teeth 83 or shallow splines. The units wheel 23 has a sleeve part 85 through which the shaft 81 runs. On the inner wall of the sleeve part 85, there are teeth 89 or shallow splines which engage with the teeth 83 on the shaft 81. The teeth 83 and 89 serve as ratchet splines of an overload clutch that limits the torque transferred between the components 23, 45. If a given torque is not exceeded, the rotation of the dosage selector 45 is transferred to the units wheel 23.

If the movement of the dose control means 49 is not blocked by the catching means 77 of the piston rod 13 or the stop means 71, 73, the rotation of the dosage selector 45 is transferred via the rotating units wheel 23 and the idler gear 19, 35 to the dose gear 43. If the dose control means 49 is blocked by the catching means 77 of the piston rod 13 or the stop means 71, 73, the torque between the shaft 81 and the units wheel 23 increases since neither the dose gear 43 nor the idler gear 19, 35 may move when the dosage selector 45 rotates. Thus, further movement of the dosage selector 45 causes slipping of the teeth 83 on the shaft over the teeth 89 inside the sleeve 85. If the user tries to select a smaller or larger dose than permitted, the dosage selector 45 can rotate due to the units wheel 23 based on a torque-activated ratchet. In other words, the rotation of the dosage selector 45 does not influence the set dose in this case.

The injection button 47 protrudes from the top of the dosage selector 45. The injection button has an elongate shaft part running through the dosages selector 45 and its hollow shaft 81. The button tip 87 protrudes from the bottom of the dosage selector's shaft 85 when the injection button 47 is pressed, which allows moving the lever arm 27 (not shown) during delivery.

Figure 10:
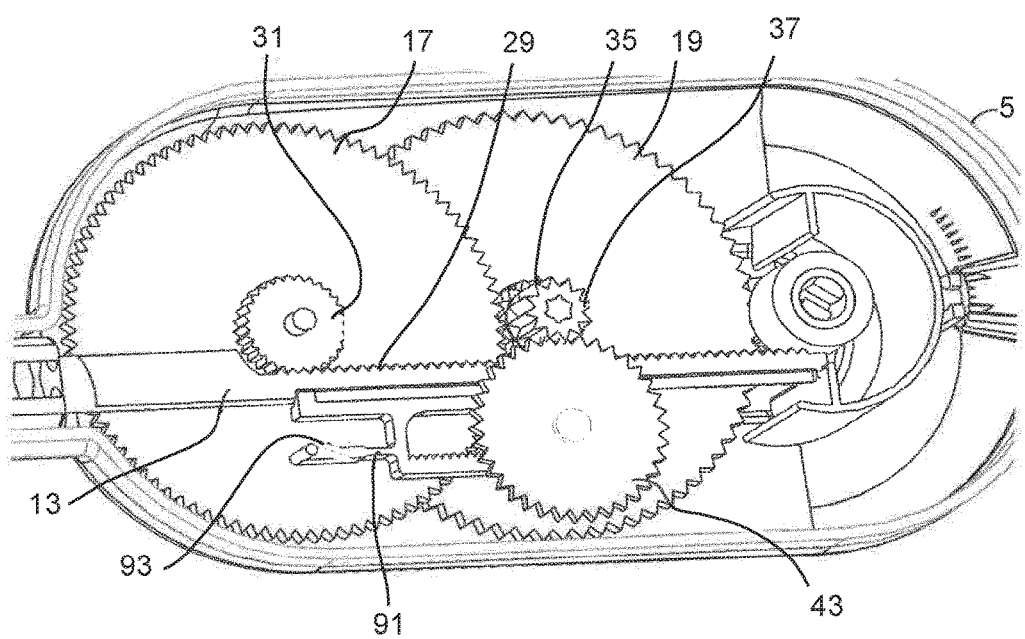
FIG. 10 shows a detailed three-dimensional front view of the drive mechanism.

FIG. 10 shows a detailed three-dimensional front view of the drive mechanism 11 in a state immediately after dose delivery. Further to the components described before, the figure shows an end-of-delivery feature 93. The end-of-delivery feature 93 is indicated by a feature on the dose control means 49 which clicks over a rib from the housing 5. Such end-of-delivery feature may be formed by an arm 91 of the dose control means that slides over the ramp-shaped rib 93 of the housing 5. The click sound may be caused when the end of the arm 91 falls over the ramp forming the end-of-delivery feature. Alternatively or additionally, the feedback may be tactile.

The intended user steps for using the delivery device are: The cap (not shown) is removed. A needle (not shown) is fitted onto the distal end of the delivery device. A priming dose, e.g. 2 IU of insulin formulation, is set by rotating the dosage selector 45. The "priming" dose is dispensed into air by pressing the injection button 47 on the proximal end of the delivery device. The required dose for delivery is dialled by rotating the dosage selector 45. The needle is inserted into the skin. The dialled dose is dispensed by pressing the injection button 47. The needle is removed from the skin. The needle is removed from the delivery device and the cap is replaced.

When the delivery device is at rest, the spring member 21 has enough preload such that, if the user selects the minimum dose, the device will be able to deliver that minimum dose. At rest, the dose indicator displays 0 or the equivalent marking to show that no dose has been selected.

Priming is the act of preparing the device for the first use, which means setting and delivering one or more small doses into the air, so that the 'play' (any clearances) and tolerances in the device are removed and components are placed into suitable compression or tension.

Safety shots are where the user sets and delivers one or more small doses into the air before each injection to ensure that the needle is not blocked.

For both priming the device and for safety shots, the user will set a small dose and inject that dose into the air until a drop of medicament is observed at the tip of the needle.

Setting a dose includes the following steps. The dose is dialed by turning the dosage selector 45, thereby rotating the units wheel 23, and per one rotation of the units wheel 23 the tens wheel 25 moves one increment. The set dose is indicated in the window 53 in the housing 5.

The act of rotating the dosage selector 45 causes a direct rotation of the units wheel 23, unless the minimum, maximum or last-dose protection is encountered, in which case the dosage selector 45 will ratchet relative to the units wheel 23 as described above.

In this embodiment, the dosage selector 45 is turned counter-clockwise for increasing the set dose.

The rotation of the units wheel 23 is transferred to the fixed and floating idler gears 19, 35, which rotate clockwise. This movement loads the spring member 21.

The rotation of the floating idler gear 35 is transferred via the dose gear 43, which rotates counter-clockwise, to an axial movement of the dose control means 49, which moves proximally with respect to the dose gear 43. The dose control means 49 ensures that the maximum dose, e.g. 120 IU of insulin formulation, is not exceeded. If the user tries to set a dose larger than the maximum dose, the end stop means 73 abuts on the dose pinion 67, thereby stopping the movement of the dose control means 49 and the idler gears 19, 35.

When the desired dose is set, delivery is initiated by pressing the injection button 47. When the injection button 47 is pressed, it has a small (~1 mm) travel against the button spring during which no action takes place. In one embodiment, the first 1.3 mm movement has no effect, which prevents accidental injection.

After that travel, several actions take place in sequence. When the injection button 47 is pressed, the tip 87 of the injection button 47 presses on the lever arm 27 which pulls the idler ratchet 64 away from the idler gear 19, thereby disengaging the idler ratchet 64 from the crown gear 63 on the fixed idler gear 19. The injection button 47 continues to pivot the lever arm 27 further, which makes the floating idler gear 35 engage with the drive gear 17 by pushing the floating idler gear 35 into mesh with the drive gear 17. In one embodiment, at 1.3 to 3 mm movement, the floating idler gear 35 is moved axially via the lever arm 27 and meshes with the drive gear 17. Since the sprung idler ratchet 64 disengages, the idler gear 19, 35 is free to rotate under the torque of the spring member 21. This means that any rotation of the fixed idler gear 19 will result in rotation of the drive gear 17 and therefore linear movement of the piston rod 13 in the distal direction. As a result, the dose is dispensed.

The spring-loaded idler gear 19 rotates counter-clockwise and is able to turn the drive gear 43, which turns clockwise. The drive gear 17, in turn, rotates clockwise and moves the piston rod 13 distally via the rack-and-pinion means 29, 31.

The spring-loaded idler gear 19, 35 also turns the dose pinion 67 in the clockwise direction, which causes distal movement of the dose control means 49.

Furthermore, the spring-loaded idler gear 19, 35 drives the units and tens wheels 23, 25 to their initial position during the delivery process.

When the delivery comes to an end, the end of injection is indicated by the arm 91 of the dose control means 49 moving up the ramp or rib forming the end-of-dose feature 93 and dropping on the other side at the end of the dose, when the dose control means 49 reaches its initial position again. The end of injection is indicated by a feature on the dose control means 49 which 'clicks' over a rib or ramp from the housing 5 at the end of the dose and the dose pinion 67 hits the hard-stopping side wall 71 of the dose rack 51.

Nevertheless, dose interruption and dose splitting is also possible.

If the injection button 47 is released mid-dose, i.e. removing the axial force of the injection button 47, the injection button 47 returns to its initial axial position relative to the dosage selector 45, and this allows the lever arm 27 to return to its initial position, which, in turn, allows the idler ratchet 64 to re-engage with the fixed idler gear 19 and prevent its rotation. As a result, the injection is stopped. Moreover, the floating idler gear 35 disengages from the drive gear 17 due to the force from the idler spring 41, which prevents further turning of the drive gear 17 and further injection. The dose can now be adjusted or the remaining dose administered. Any further change in the set dose will not move the piston rod 13 until the injection button 47 is fully depressed again.

The dose can be changed by rotating the dosage selector 47, and pressing the injection button 47 restarts the injection manoeuvre.

After delivery, it may be beneficial that the needle is not removed from the skin immediately but remains there for a hold time. The "hold time" is the period from when the mechanism has stopped moving, most typically indicated by the dose indicator reaching zero, to when the dose is fully delivered and the user can remove the needle from the patient without affecting the delivered dose volume.

Hold time is required on some devices because, if the user injects the drug too fast, it can take some time, typically a few seconds, for the elasticity of the mechanics to equilibrate and deliver the correct volume and for the drug formulation to disperse in the tissue and reduce the back pressure.

The ratios of the gears are chosen in such a manner that they give direct translation from the dosage selector 45 to the units wheel 23 and to the dose rack 51 and the drive gear 17. The dose control means 49 moves at the same ratio as the piston rod 13, which allows a simple interaction to achieve last-dose protection.

In this embodiment, the delivery device is entirely driven by the spring member 21, which means that the injection speed should be much less variable than for a manual device. If the maximum injection speed is consistent and minimized, the hold time may be reduced. The injection speed is inherently controlled for a low and consistent hold time.

The delivery device may be assembled by a simple process. The lever arm 27 and the spring idler ratchet 64 are positioned in the lower case 54. The escapement gear 28 is placed in the lower case 54. The idler gear subassembly, including the spring member 21, the idler spring 41, the idler gears 19, 35, are positioned in the lower case 54. The drive gear 17 and the cartridge and piston rod subassembly 7, 13, wherein the piston rod 13 is in a fully retracted position, are positioned in the lower case 54.

The counter subassembly, including the injection button 47, the dosage selector 45 and the units and tens wheels 23, 25 are assembled in the upper case 6. The dose control means 49 and the dose gear 43 are assembled in the upper case 6. The upper and lower subassemblies are aligned. Pressure is applied to clip the parts together. The device could be primed in assembly.

During assembly, most of the components can be placed into the lower case 54. If the cartridge 7 is the last component to be placed into the lower case 54, the mechanism could be set so that the clearances are minimal or even zero. Then the upper case can be added. This means that the number of priming shots and therefore the number of user steps required to prime the device is minimised.

The device is designed to be disposable (in that the cartridge 7 cannot be replaced by the user or healthcare professional), but a reusable type of the device could be created by making the cartridge holder removable and allowing the resetting of the piston rod 13.

The front-mounted dosage selector 45 and injection button 47, which allow comfortable use and require low dose setting torque, could be used in any device which requires a variable to be set and then a trigger, or reset, action to be performed. Examples include drug delivery devices such as pen injectors, detergent dispensers, and hopper-based dispensers, which may be used for products such as sweets (confectionaries), coffee beans, or drinks such as alcoholic spirits.

The delivery device having a flat odometer has an ergonomic form factor and a comfortable shape. The unusual form allows a differentiation due to the shape and the position of the dose selector and the injection button.

The efficient rack-and-pinion mechanism could be applied to any device which dispenses a fluid (liquid or gas) or powder from a container by translating a piston rod. Examples of devices which may be provided with such a mechanism include drug delivery devices such as pen injectors or auto-injectors; medical devices such as dispensers of antiseptic creams, analgesic creams, detergents and so on. The mechanism may be used in devices for dispensing adhesives, lubricants, paints, detergents and suchlike. These could be used in professional applications such as engineering workshops or in consumer applications such as 'do it yourself' products or 'fast moving consumer goods'. The mechanism may also be used in food dispensers for non-rigid foods such as tomato sauce, crushed garlic, cheese, butter, juice, smoothie, soup, coffee, tea, jam, peanut butter and so on.

The features of the embodiments mentioned above may be combined. The layout, function, and number of components may be changed in other embodiments.

REFERENCE NUMERALS 1 arrow (distal direction)
3 arrow (proximal direction)
5 housing
6 upper case
7 cartridge
9 bung
11 drive mechanism
13 piston rod
17 drive gear
19 fixed idler gear
21 spring member
23 units wheel
25 tens wheel
27 lever arm
28 escapement gear
29 rack
31 pinion
33 shaft
35 floating idler gear
37 toothed wheel
39 toothed wheel
41 idler spring
43 dose gear
45 dosage selector
47 injection button
49 dose control means
51 rack
53 window
54 lower case
55 crown gear
57 set of teeth
59 notch features
61 ribs
62 recess
63 crown gear
64 idler ratchet 65 leg
67 pinion
69 slot
71 stop means
73 stop means
77 catching means
79 catching means
81 shaft
83 teeth
85 sleeve part
87 rib
89 teeth
91 arm
93 end-of-delivery feature

The invention claimed is:

1. A drive mechanism for a delivery device, the drive mechanism comprising:
a drive member for driving a piston rod;
a moveable dose setting member being disengaged from the drive member in a dose setting state and being moveable in a drive direction in a dose delivery state, wherein the dose setting member engages with the drive member in the dose delivery state in such a manner that a movement of the dose setting member in the drive direction is transferred to the drive member; and
a spring member being coupled to the dose setting member in such a manner that the movement of the dose setting member in a setting direction loads the spring member in the dose setting state, a spring force of the loaded spring member driving the dose setting member in the drive direction in the dose delivery state,
wherein the drive member comprises a drive gear and the dose setting member comprises a floating gear and a further gear, the floating gear being non-rotatably coupled to the further gear, wherein the floating gear is moveable along a rotational axis of the floating gear with respect to the further gear in such a manner that the floating gear disengages from the drive gear in the dose setting state and engages with the drive gear in the dose delivery state.

2. The drive mechanism according to claim 1, further comprising a ratchet mechanism preventing movement of the dose setting member in the drive direction that is caused by the spring force in the dose setting state.

3. The drive mechanism according to claim 1, wherein the spring member comprises a flat torsion spring.

4. The drive mechanism according to claim 3, wherein the flat torsion spring is arranged adjacent to a face side of the further gear.

5. The drive mechanism according to claim 1, wherein the drive member is coupled to the piston rod by a rack-and-pinion mechanism.

6. The drive mechanism according to claim 1, further comprising a rotatable dosage selector coupled to the dose setting member in such a manner that a rotational movement of the dosage selector is transferred to the dose setting member in the dose setting state.

7. The drive mechanism according to claim 6, wherein the dosage selector is coupled to a units wheel and a tens wheel, the tens wheel being coupled to the units wheel by an escapement gear, the units wheel indicating units of a set dose, the tens wheel indicating tens of the set dose.

8. The drive mechanism according to claim 6, further comprising:
a dose control mechanism that is coupled to the dose setting member in such a manner that the dose setting member is blocked when a maximum or minimum dose is set; and
a ratchet mechanism preventing transmission of movement from the dosage selector to the dose setting member when the dose setting member is blocked.

9. The drive mechanism according to claim 1, further comprising a button member coupled to the dose setting member in such a manner that pressing the button member causes the dose setting member to be engaged with the drive member.

10. The drive mechanism according to claim 9, further comprising a lever arm which is suitable to move the floating gear such that the floating gear engages with the drive member when the button member is pressed.

11. The drive mechanism according to claim 10, further comprising a ratchet mechanism preventing movement of the dose setting member in the drive direction that is caused by the spring force in the dose setting state, wherein the ratchet mechanism is connected to the lever arm, the ratchet mechanism engaging with the dose setting member in the dose setting state, thereby preventing the spring force from moving the dose setting member.

12. The drive mechanism according to claim 9, wherein the dose setting member is a dosage selector, and the button member is located axisymmetrically with the dosage selector.

13. The drive mechanism according to claim 1, further comprising at least one dose setting wheel being suitable for providing tactile feedback, audible feedback, or tactile feedback and audible feedback.

14. A drug delivery device comprising:
a housing; and
a drive mechanism at least partially within the housing, the drive mechanism comprising:
a drive member for driving a piston rod,
a moveable dose setting member being disengaged from the drive member in a dose setting state and being moveable in a drive direction in a dose delivery state, wherein the dose setting member engages with the drive member in the dose delivery state in such a manner that a movement of the dose setting member in the drive direction is transferred to the drive member, and
a spring member being coupled to the dose setting member in such a manner that the movement of the dose setting member in a setting direction loads the spring member in the dose setting state, a spring force of the loaded spring member driving the dose setting member in the drive direction in the dose delivery state,
wherein the drive member comprises a drive gear and the dose setting member comprises a floating gear and a further gear, the floating gear being non-rotatably coupled to the further gear, wherein the floating gear is moveable along a rotational axis of the floating gear with respect to the further gear in such a manner that the floating gear disengages from the drive gear in the dose setting state and engages with the drive gear in the dose delivery state.

15. The drug delivery device according to claim 14, wherein the housing comprises an upper case and a lower case.

16. The drug delivery device according to claim 15, wherein the upper case and the lower case are joined along a substantially planar interface, wherein the normal to a plane in which the interface lies is more than 45 degrees from an axis of a cartridge in the housing.

17. A drive mechanism for a delivery device, the drive mechanism comprising:
- a drive member for driving a piston rod;
- a moveable dose setting member being disengaged from the drive member in a dose setting state and being moveable in a drive direction in a dose delivery state, wherein the dose setting member engages with the drive member in the dose delivery state in such a manner that a movement of the dose setting member in the drive direction is transferred to the drive member;
- a spring member being coupled to the dose setting member in such a manner that the movement of the dose setting member in a setting direction loads the spring member in the dose setting state, a spring force of the loaded spring member driving the dose setting member in the drive direction in the dose delivery state;
- a button member coupled to the dose setting member in such a manner that pressing the button member causes the dose setting member to be engaged with the drive member; and
- a lever arm which is suitable to move a floating gear such that the floating gear engages with the drive member when the button member is pressed.

* * * * *